US006794318B2

(12) United States Patent
Anderson et al.

(10) Patent No.: US 6,794,318 B2
(45) Date of Patent: Sep. 21, 2004

(54) USE-DEPENDENT INDICATOR SYSTEM FOR ABSORBENT ARTICLES

(75) Inventors: Ralph L. Anderson, Marietta, GA (US); James W. Clark, Roswell, GA (US); Fred R. Radwanski, Stone Mountain, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 96 days.

(21) Appl. No.: 09/746,719

(22) Filed: Dec. 22, 2000

(65) Prior Publication Data

US 2001/0031595 A1 Oct. 18, 2001

Related U.S. Application Data

(60) Provisional application No. 60/173,344, filed on Dec. 28, 1999.

(51) Int. Cl.$^7$ .......................... B32B 27/04; B32B 27/12
(52) U.S. Cl. .................. 442/123; 106/15.05; 106/31.13
(58) Field of Search ........................... 442/123, 71, 73, 442/414; 106/15.05, 31.13, 31.27

(56) References Cited

U.S. PATENT DOCUMENTS

| | | | |
|---|---|---|---|
| 2,449,274 A | 9/1948 | Broll | 167/33 |
| 2,542,909 A | 2/1951 | De Wet | 167/84 |
| 2,702,780 A | 2/1955 | Lerner | 167/84 |
| 3,060,078 A | 10/1962 | Pattilloch | 162/161 |
| 3,400,420 A | 9/1968 | Granville et al. | 15/104.93 |
| 3,640,841 A | 2/1972 | Winslow et al. | 162/164 |
| 3,663,262 A | 5/1972 | Cogan, Jr. | 117/62.1 |
| 3,704,096 A | 11/1972 | Verses et al. | 23/230 R |
| 3,857,934 A | 12/1974 | Bernstein et al. | 424/30 |
| 3,983,209 A | 9/1976 | Schmitt | 424/78 |
| 4,045,364 A | 8/1977 | Richter | 252/106 |
| 4,064,213 A | 12/1977 | Lazorisak et al. | 264/134 |
| 4,102,998 A | 7/1978 | Gutnick | 424/15 |
| 4,125,659 A | 11/1978 | Klowak et al. | 428/153 |
| 4,188,447 A | 2/1980 | Ehlenz | 428/310 |
| 4,205,043 A | 5/1980 | Esch et al. | 422/56 |
| 4,248,597 A | 2/1981 | McNeely | 23/230 R |
| 4,311,479 A | 1/1982 | Fenn et al. | 8/495 |
| 4,323,557 A | 4/1982 | Rosso et al. | 424/28 |
| 4,343,788 A | 8/1982 | Mustacich et al. | 424/78 |
| 4,392,908 A * | 7/1983 | Dehnel | 427/194 |
| 4,404,196 A | 9/1983 | Daudt et al. | 424/184 |
| 4,424,060 A | 1/1984 | Nakamura et al. | 8/115.5 |
| 4,436,780 A | 3/1984 | Hotchkiss et al. | 428/198 |
| 4,443,222 A | 4/1984 | Morris et al. | 8/189 |
| 4,454,110 A | 6/1984 | Caslavsky et al. | 424/54 |
| 4,496,322 A | 1/1985 | Sandham et al. | 433/217 |
| 4,504,442 A | 3/1985 | Rosenblatt et al. | 422/37 |
| 4,515,703 A | 5/1985 | Haq | 252/92 |
| 4,533,435 A | 8/1985 | Intili | 162/161 |
| 4,547,381 A | 10/1985 | Mason et al. | 426/316 |
| 4,563,184 A | 1/1986 | Korol | 604/368 |
| 4,563,351 A | 1/1986 | Caslavsky et al. | 424/151 |
| 4,568,535 A | 2/1986 | Loesche | 424/19 |
| 4,568,536 A | 2/1986 | Kronenthal et al. | 424/22 |
| 4,615,697 A | 10/1986 | Robinson | 604/890 |
| 4,615,705 A | 10/1986 | Scales et al. | 623/11 |
| 4,615,937 A | 10/1986 | Bouchette | 428/288 |
| 4,659,609 A | 4/1987 | Lamers et al. | 428/194 |
| 4,661,344 A | 4/1987 | Relenyi | 424/79 |
| 4,668,228 A | 5/1987 | Bolton et al. | 604/307 |
| 4,675,347 A | 6/1987 | Mochizuki et al. | 523/122 |
| 4,678,704 A | 7/1987 | Fellows | 428/289 |
| 4,681,739 A | 7/1987 | Rosenblatt et al. | 422/37 |
| 4,689,169 A | 8/1987 | Mason et al. | 252/186.24 |
| 4,692,374 A | 9/1987 | Bouchette | 428/288 |
| 4,725,271 A | 2/1988 | Korol | 604/368 |
| 4,728,498 A | 3/1988 | Theeuwes | 422/29 |
| 4,735,739 A | 4/1988 | Floyd et al. | 252/91 |
| 4,736,467 A | 4/1988 | Schwarze et al. | 2/114 |
| 4,737,405 A | 4/1988 | Bouchette | 428/288 |
| 4,740,398 A | 4/1988 | Bouchette | 428/28 |
| 4,772,492 A | 9/1988 | Bouchette | 427/342 |
| 4,781,974 A | 11/1988 | Bouchette et al. | 428/288 |
| 4,810,567 A | 3/1989 | Calcaterra et al. | 428/224 |
| 4,833,003 A | 5/1989 | Win et al. | 428/198 |
| 4,835,019 A | 5/1989 | White et al. | 427/387 |
| 4,837,079 A | 6/1989 | Quantrille et al. | 428/288 |
| 4,847,089 A | 7/1989 | Kramer et al. | 424/405 |
| 4,882,167 A | 11/1989 | Jang | 424/468 |
| 4,883,828 A | 11/1989 | Oakes et al. | 523/122 |
| 4,906,464 A | 3/1990 | Yamamoto et al. | 424/78 |
| 4,908,209 A | 3/1990 | McIntosh, Jr. et al. | 424/409 |
| 4,908,381 A | 3/1990 | Greenwald et al. | 514/460 |
| 4,917,686 A | 4/1990 | Bayston et al. | 604/265 |
| 4,929,498 A | 5/1990 | Suskind et al. | 428/288 |
| 4,938,955 A | 7/1990 | Niira, deceased et al. | 424/79 |

(List continued on next page.)

FOREIGN PATENT DOCUMENTS

| | | | | |
|---|---|---|---|---|
| DE | 2625176 B2 | 12/1977 | | C11D/17/04 |
| DE | 2838523 A1 | 3/1980 | | A47K/3/00 |
| EP | 0080382 A2 | 6/1983 | | D04H/1/56 |

(List continued on next page.)

OTHER PUBLICATIONS

International Search Report dated Apr. 23, 2001 for International Application No. PCT/US00/34932.

(List continued on next page.)

*Primary Examiner*—Terrel Morris
*Assistant Examiner*—Arden B. Sperty
(74) *Attorney, Agent, or Firm*—Dority & Manning, P.A.

(57) ABSTRACT

A use-dependent indicator system for detecting the exhaustion of an active chemical within an absorbent article is provided. The indicator system includes at least one dye component and a polymer mixture. The dye component(s) can be non-reactive and/or reactive dyes. The polymer mixture can contain a polymer, such as a latex adhesive, to facilitate control over the dissolution rate of the dye component(s). By controlling the dissolution rate of the dye component(s), an indicator system of the present invention can impart a change in color to signal the exhaustion of an active chemical incorporated within the absorbent article, such as an anti-microbial agent.

10 Claims, No Drawings

U.S. PATENT DOCUMENTS

| | | | |
|---|---|---|---|
| 4,938,958 A | 7/1990 | Niira, deceased et al. | 424/79 |
| 4,990,144 A | 2/1991 | Blott | 604/304 |
| 4,997,425 A | 3/1991 | Shioya et al. | 604/304 |
| 4,999,386 A | 3/1991 | Oakes et al. | 523/122 |
| 5,006,339 A | 4/1991 | Bargery et al. | 424/404 |
| 5,011,602 A | 4/1991 | Totani et al. | 210/484 |
| 5,019,096 A | 5/1991 | Fox, Jr. et al. | 623/1 |
| 5,023,089 A | 6/1991 | Sakamoto et al. | 424/502 |
| 5,027,438 A | 7/1991 | Schwarze et al. | 2/114 |
| 5,037,843 A | 8/1991 | Schoenberg | 514/389 |
| 5,061,485 A | 10/1991 | Oakes et al. | 424/81 |
| 5,069,907 A | 12/1991 | Mixon et al. | 424/445 |
| 5,071,648 A | 12/1991 | Rosenblatt | 424/78.06 |
| 5,087,450 A | 2/1992 | Lister | 424/402 |
| 5,108,740 A | 4/1992 | Greenwald et al. | 424/78.32 |
| 5,120,813 A | 6/1992 | Ward, Jr. | 528/28 |
| 5,126,070 A | 6/1992 | Leifheit et al. | 252/186.36 |
| 5,133,090 A | 7/1992 | Modak et al. | 2/168 |
| 5,149,469 A | 9/1992 | Komatsuzaki et al. | 264/28 |
| 5,154,920 A | 10/1992 | Flesher et al. | 514/643 |
| 5,158,778 A | 10/1992 | Donovan et al. | 424/488 |
| 5,173,535 A | 12/1992 | Abrutyn | 525/54.3 |
| 5,178,870 A | 1/1993 | Schaeken et al. | 424/405 |
| 5,211,959 A | 5/1993 | Yoshii et al. | 424/489 |
| 5,213,884 A | 5/1993 | Fellows | 428/240 |
| 5,226,434 A | 7/1993 | Britton et al. | 132/321 |
| 5,227,168 A | 7/1993 | Chvapil et al. | 421/445 |
| 5,236,703 A | 8/1993 | Usala | 424/78.36 |
| 5,238,843 A | 8/1993 | Carpenter et al. | 435/264 |
| 5,242,985 A | 9/1993 | Shih et al. | 525/326.9 |
| 5,266,329 A | 11/1993 | Riley, Jr. | 424/430 |
| 5,284,703 A | 2/1994 | Everhart et al. | 428/283 |
| 5,290,393 A | 3/1994 | Nakamura | 156/613 |
| 5,293,648 A | 3/1994 | Finley | 2/243.1 |
| 5,298,252 A | 3/1994 | Hagiwara et al. | 424/409 |
| 5,317,987 A | 6/1994 | Muller et al. | 116/206 |
| 5,320,806 A | 6/1994 | Dziabo et al. | 422/29 |
| 5,322,695 A | 6/1994 | Shah et al. | 424/448 |
| 5,324,520 A | 6/1994 | Dunn et al. | 424/435 |
| 5,330,746 A | 7/1994 | Friedman et al. | 424/49 |
| 5,336,505 A | 8/1994 | Ng et al. | 424/486 |
| 5,340,581 A | 8/1994 | Tseng et al. | 424/401 |
| 5,344,411 A | 9/1994 | Domb et al. | 604/265 |
| 5,350,624 A | 9/1994 | Georger et al. | 428/219 |
| 5,356,803 A | 10/1994 | Carpenter et al. | 435/200 |
| 5,366,732 A | 11/1994 | Zighelboim R | 424/411 |
| 5,368,852 A | 11/1994 | Umemoto et al. | 424/78.1 |
| 5,378,475 A | 1/1995 | Smith et al. | 424/473 |
| 5,389,202 A | 2/1995 | Everhart et al. | 162/103 |
| 5,407,685 A | 4/1995 | Malchesky et al. | 424/449 |
| 5,408,022 A | 4/1995 | Imazato et al. | 526/259 |
| 5,413,788 A | 5/1995 | Edwards et al. | 424/409 |
| 5,421,898 A | 6/1995 | Cavanagh | 134/7 |
| 5,429,854 A | 7/1995 | Currie et al. | 428/138 |
| 5,432,000 A | 7/1995 | Young, Sr. et al. | 428/372 |
| 5,486,381 A | 1/1996 | Cleveland et al. | 427/294 |
| 5,487,896 A | 1/1996 | Modak et al. | 424/78.17 |
| 5,503,840 A | 4/1996 | Jacobson et al. | 424/421 |
| 5,536,768 A | 7/1996 | Kantner et al. | 524/376 |
| 5,554,373 A | 9/1996 | Seabrook et al. | 424/400 |
| 5,556,699 A | 9/1996 | Niira, deceased et al. | 428/323 |
| 5,565,361 A | 10/1996 | Mutsakis et al. | 435/299.1 |
| 5,573,841 A | 11/1996 | Adam et al. | 428/219 |
| 5,578,124 A | 11/1996 | Cleveland et al. | 118/50 |
| 5,578,315 A | 11/1996 | Chien et al. | 424/435 |
| 5,584,877 A | 12/1996 | Miyake et al. | 623/1 |
| 5,603,921 A | 2/1997 | Bowen | 424/49 |
| 5,611,938 A | 3/1997 | Smolik et al. | 210/755 |
| 5,612,052 A | 3/1997 | Shalaby | 424/426 |
| 5,614,223 A | 3/1997 | Sipos | 424/489 |
| 5,616,315 A | 4/1997 | Masterman et al. | 424/54 |
| 5,629,081 A | 5/1997 | Richards et al. | 442/96 |
| 5,648,003 A | 7/1997 | Liang et al. | 219/211 |
| 5,652,274 A | 7/1997 | Martin | 514/724 |
| 5,656,361 A | 8/1997 | Vogt et al. | 428/198 |
| 5,681,575 A | 10/1997 | Burrell et al. | 424/423 |
| 5,686,065 A | 11/1997 | Haney | 424/59 |
| 5,695,857 A | 12/1997 | Burrell et al. | 428/209 |
| 5,699,326 A | 12/1997 | Haas et al. | 368/327 |
| 5,702,992 A | 12/1997 | Martin et al. | 442/123 |
| 5,707,736 A | 1/1998 | Levy et al. | 428/375 |
| 5,723,132 A | 3/1998 | Tseng et al. | 424/401 |
| 5,730,994 A | 3/1998 | Askill et al. | 424/402 |
| 5,733,503 A | 3/1998 | Kowatsch et al. | 422/28 |
| 5,736,473 A | 4/1998 | Cohen et al. | 442/239 |
| 5,744,150 A | 4/1998 | Cercone | 424/404 |
| 5,747,078 A | 5/1998 | De Jong et al. | 426/9 |
| 5,753,251 A | 5/1998 | Burrell et al. | 424/426 |
| 5,763,412 A | 6/1998 | Khan et al. | 514/23 |
| 5,770,182 A | 6/1998 | Fischer | 424/49 |
| 5,770,255 A | 6/1998 | Burrell et al. | 427/2.1 |
| 5,807,563 A | 9/1998 | Askill et al. | 424/402 |
| 5,811,113 A | 9/1998 | Dorr et al. | 424/404 |
| 5,817,325 A | 10/1998 | Sawan et al. | 424/411 |
| 5,820,607 A | 10/1998 | Tcholakian et al. | 604/265 |
| 5,827,925 A | 10/1998 | Tremont et al. | 525/102 |
| 5,829,442 A | 11/1998 | Cox et al. | 128/849 |
| 5,834,051 A | 11/1998 | Woloszko et al. | 427/2.24 |
| 5,837,274 A | 11/1998 | Shick et al. | 424/406 |
| 5,837,275 A | 11/1998 | Burrell et al. | 424/409 |
| 5,840,674 A | 11/1998 | Yatvin et al. | 514/2 |
| 5,849,311 A | 12/1998 | Sawan et al. | 424/406 |
| 5,851,551 A | 12/1998 | Tseng et al. | 424/486 |
| 5,853,760 A | 12/1998 | Cremer | 424/484 |
| 5,853,859 A | 12/1998 | Levy et al. | 428/196 |
| 5,855,208 A | 1/1999 | Askill et al. | 128/849 |
| 5,856,364 A | 1/1999 | Martin | 514/724 |
| 5,874,098 A | 2/1999 | Stevens et al. | 424/408 |
| 5,891,811 A | 4/1999 | Ashida et al. | 442/71 |
| 5,990,199 A * | 11/1999 | Bealing et al. | 523/161 |

FOREIGN PATENT DOCUMENTS

| | | | | |
|---|---|---|---|---|
| EP | 0113254 A1 | 11/1984 | | D04H/1/58 |
| EP | 0351907 A2 | 1/1990 | | A01N/25/34 |
| EP | 0259113 B1 | 10/1990 | | A61K/9/22 |
| EP | 0407943 A1 | 1/1991 | | A61F/13/00 |
| EP | 0280571 B1 | 4/1993 | | A61K/9/22 |
| EP | 0285209 B1 | 5/1993 | | A01N/37/34 |
| EP | 0351580 B1 | 5/1993 | | A61K/9/22 |
| EP | 0290676 B1 | 8/1994 | | C09D/133/00 |
| EP | 0265906 B1 | 4/1995 | | A61F/13/00 |
| EP | 0677296 A2 | 10/1995 | | A61L/2/20 |
| EP | 0709507 A1 | 1/1996 | | D04H/1/64 |
| EP | 0518445 B1 | 4/1996 | | A23L/3/3571 |
| EP | 0552151 B1 | 3/1997 | | A61K/31/74 |
| EP | 0761243 A1 | 3/1997 | | A61L/29/00 |
| EP | 0537774 B1 | 1/1998 | | A61K/6/083 |
| EP | 0838224 A2 | 4/1998 | | A61K/47/48 |
| EP | 0852148 A1 | 7/1998 | | A61L/15/46 |
| EP | 0869216 A1 | 7/1998 | | D06M/16/00 |
| EP | 0858810 A2 | 8/1998 | | A61L/25/00 |
| EP | 0861659 A1 | 9/1998 | | A61K/9/32 |
| EP | 0866103 A1 | 9/1998 | | C09D/5/14 |
| EP | 0875146 A1 | 11/1998 | | A01N/59/16 |
| EP | 0600004 B1 | 12/1998 | | A46B/11/00 |
| EP | 0890336 A1 | 1/1999 | | A47L/13/17 |
| EP | 0565301 B1 | 2/1999 | | A61K/47/48 |
| FR | 2431570 | 2/1980 | | D21H/5/22 |
| GB | 2211092 A | 6/1989 | | A01N/25/34 |
| JP | 1311008 | 12/1989 | | A01N/61/00 |
| WO | WO 89/05093 | 6/1989 | | A01N/25/34 |

| | | | | |
|---|---|---|---|---|
| WO | WO 90/02166 | 8/1990 | ........... | C11D/17/04 |
| WO | WO 91/03938 | 4/1991 | ........... | A01N/25/24 |
| WO | WO 92/22221 | 12/1992 | ........... | A23L/3/3571 |
| WO | WO 94/26317 | 11/1994 | ........... | A61L/2/16 |
| WO | WO 95/13704 | 5/1995 | ........... | A01N/59/16 |
| WO | WO 95/11666 | 4/1996 | ........... | A61K/7/16 |
| WO | WO 96/40361 | 12/1996 | ........... | A61M/39/16 |
| WO | WO 98/24890 | 6/1998 | ........... | C12N/9/02 |
| WO | WO 98/44962 | 10/1998 | ........... | A61L/25/00 |

OTHER PUBLICATIONS

International Search Report dated Apr. 18, 2001 for International Application No. PCT/US00/34930.

Dialog Abstract 00423532/7 © 1998 of Japanese Patent JP 8205762A published Aug. 13, 1996 entitled Antimicrobial Functional Sheet For Preserving Animal Protein.

Dialog Abstract 008079373/7 © 1998 of Japanese Patent JP 1257124A published Oct. 13, 1989 entitled Antibiotic Aluminosilicate—Obtd. by Ion Exchange of Ions in Aluminosilicate to Alkaline Earth or Manganese Ions.

Dialog Abstract 009133362 ©0 1999 of EP 497350A1 published Aug. 5, 1992 entitled Crystal Growth on Nitride Semiconductor Having Nitride Buffer Layer for Improved Crystallinity of Semiconductor Growth Giving Improved Electrical Performance.

Dialog Abstract 011141997 © 1999 of CN 1080833A published Jan. 19, 1994 entitled Wet Toilet Paper and Preparing Method Thereof.

Dialog Abstract 008146353 © 1999 of Japanese Patent JP 1311008A published Dec. 15, 1989 entitled Antibiotics and Antifungal Compsn.—Comprises Zeolite Contg. Antibiotic Metal Ion and Resin e.g. Acryl for Processing.

Dialog Abstract 01824797/7 © 1998 of U.S. Pat. No. 4,882,167 published Nov. 21, 1989 entitled Dry Direct Compression Compositions for Controlled Release Dosage Forms [Matrix of Hydrophobic Carbohydrate Polymer, Digestive Difficulty Soluble Wax, Fatty Acid or Neutral Lipid.]

Dialog Abstract 004062594 © 1999 of DE 3305265A published Aug. 16, 1984 entitled Hygienic Toilet Seat Cover for One–Time Uuse—Comprises Piece of Crepe Toilet Paper Cut to Shape of Seat and Provided with Self–Adhesive Strips for Attachment to Seat.

WPI Acc No. 97–200913/199718 Abstract of U.S. Pat. No. 5,118,509A entitled Inducing Skin Tolerance to Sensitising Drug—by Continuously and Co–Extensively Administering Drug with Corticosteroid, Preferably Hydrocortisone, to Selected Site.

Dialog Abstract 002274528 © 1999 of DE 2813421A published Oct. 4, 1979 entitled Perforated Multiple Crepe Paper and Tissue Mat Assembly—Sprayed with Antimycotic Disinfectant and Supported on Abrasion–Resistant Backing.

Dialog Abstract 05750225/9 © 1999 entitled New Antimicrobial Agent to be Included in Stainless Steel Products.

Dialog Abstract 00365165/7 © 1998 of Japanese Patent JP 7123963A published May 16, 1995 entitled Antimicrobial Water Absorbing Sheet.

Dialog Abstract 00162494/7 © 1998 of West German Patent EP 206285 published Jun. 27, 1985 entitled Filter Cartridge for Upgrading Drinking Water Quality.

Dialog Abstract 008153158/7 © 1998 of Japanese Patent JP 1316303A published Dec. 21, 1989 entitled Hydrous Antimicrobial Agent—Comprises Inorganic Carrier Contg. Antimicrobial Agent and Nonwoven Fabric of e.g. Polyester Resin Layer.

Abstract 009382194 of U.S. Pat. No. 5,186,927A published Feb. 16, 1993 entitled Antimicrobiol Compsn. for Oral Hygiene—Comprises Particles Having an Outer Surface onto Which Antimicrobial Agent has been Adsorbed.

Derwent Abstract 010600920 © 1999 of Patent AU 9514811A published Jan. 25, 1996 entitled Antimicrobial Laminate for Bags for Foodstuffs for Gradual Release—Ccomprises Substrate Impervious to Steam and Pervious Firm Superposed Through Adhesive Layer Contg. Polyallyl Isothiocyanate Cyclodextrin Cpd.

Abstract 009382274 of U.S. Pat. No. 5,187,158A published Feb. 16, 1993 entitled New O–dihydropyridylcarbonyl Prodrug Derivs. of Ribovarin–Used for Site Specific and Sustained Delivery of Antiviral Agent to the Brain, and is Retained in the Brain After Oxidn. to Quat. Pyridinium Form.

Abstract 009230315 of CA Patent 1307738C published Sep. 22, 1992 entitled Liposome(s) Having Out Bilayer with Asymmetric Distribution—Comprise Ionisable Lipid or Ionisable Protein, Useful as a Drug Delivery Systems.

Abstract 008636625 of CA Patent 2020966A published Jan. 13, 1991 entitled Biocompatible Film–Forming Topical Delivery System—Comprises Active Salt of Carboxylic Acid–Functional Polymer with Therapeutic Agent.

Dialog Abstract 010620478 © 1999 of CA 2134498A published Nov. 26, 1995 entitled Cove Base for Building Wall—Has Elongate Flat Plate Containing Antimicrobial Agent Released Over Time.

Abstract 003667575 of DE 3134152A published Mar. 17, 1983 entitled Antimicrobial Carrier Esp. for Delivery to Bone—is Metal or Plastics Coil Opt. with Polymer Coating.

Abstract 004653629 of EP 184629 A published Jun. 18, 1986 entitled Microbicidal Tub for Urine Drainage Bag—Passively Releases Antimicrobial on Emptying to Prevent Infection.

Dialog Abstract 009588282 © 1999 of EP 558913 A1 published Sep. 9, 1993 entitled Two Component Minocycline Controlled Release Delivery System—Comprises Initial Loading of Rapid Release Granules and Sec. Loading of Blended Polymer Coated Spherical Granules.

Dialog Abstract 011058050 © 1999 of EP 748634 A2 published Dec. 18, 1996 entitled Surgical Implant, Esp. for Use as Vascular Prosthesis—Produced from or Comprising Resorbable Material Contg. Antimicrobial Agent, Esp. Gentamycin Crobefate.

Abstract 004440566 © 1999 of JP 60181029 A published Sep. 14, 1985 entitled Sustained Release Drug. Prepn.—Involves Mixing a e.g. Peptide, Protein, Antimicrobial or Antitumor Drug with Lactic Acide (co) Polymer.

Abstract 008370474 © 1999 of JP 2180694 A published Jul. 13, 1990 entitled Contimination Preventing System for Sterile Water Producing System—Includes Container Contg. Gradual Release Alkali Cpd. and Having Discharge Opening Dia. Preventing Contamination.

Abstract 009176092 © 1999 of JP 4208205A published Jul. 29, 1992 entitled Sustained Release Antimicrobial Ally Isothiocyanate Compsn.—Prepd. by Dissolving Allyl Isothiocyanate in Glycerine Ester or High Alcohol Ester.

Abstract 010615628 © 1999 of JP 8012511A published Jan. 16, 1996 entitled Prodn. of Sustained–Release Antimicrobial Agent Used to Maintain Freshness of e.g. Processed Food—Comprises Dissolving Volatile Antimicrobial Component in Organic Solvent, Adding Starch and Removing Solvent.

Abstract 010853168 of JP 8165210 A published Jun. 25, 1996 entitled Prodn. of Antimicrobial Agents—Involves Radically Polymerising Poly(meth)acryllic Acid Ester Cpds. in Organic Solvent Contg. Aq. Soln. of Silver, Copper or Zinc Ions.

Abstract 010853169 of JP 8165211A published Jun. 25, 1996 entitled Prodn. of antimicrobial Agents—Copolymerising Polyacrylic or Polymethacryclic Acid Ester Cpds. and Silver, Copper or Zinc (Meth) Acrylic Acid Salts, Inorganic Solvent.

Dialog Abstract 011029508 of JP 8277204A published Oct. 22, 1996 entitled Sustained Release Microorganism Control Prepn—Prepd by Coating Liq Drop Contg Microorganism Control Agent with Hydrophobic until Microparticle Silicon Oxide Power.

Abstract 011665622 of JP 9315927A published Dec. 9, 1997 entitled Antimicrobial Cosmetic—Comprises Water Containing Components Released from Copper or Copper Alloy at Effective Doses Which Give Antimicrobial Activity.

Abstract 011393337 of Russian Patent RU 2071323C1 published Jan. 10, 1997 entitled Antiviral Sustained Release Preparation for Treating Acute Respiratory Diseases and Herpes—Contg. Salt Based on Adamantyl–Methylamine Cpd. and Copolymer Derived from Vinyl Alcohol and N–Vinylamidosuccinic Acid.

Abstract 007135943 of WO 8702576A published May 7, 1987 entitled Vaginal Delivery Systems—Consist of Viscous Emulsion with (Non)lipoidal Phases, which Adheres to Vaginal Wall.

Abstract 007673497 of WO 8807853A published Oct. 20, 1988 entitled Lipsomal Vesicles for Sustained Intraperitoneal Delivery—Comprise Therapeutic Agent Encapsulated in Phosphatidyl Choline–Contg. Lipid Vesicle.

Abstract 009122425 of WO 9211042 A1 published Jul. 9, 1992 entitled Compsns, for Disinfecting Contact Lenses–Comprising Aq. Hydrogen Peroxide, and a Hydrogen Peroxide–Reducing Agent to Enhance Antimicrobial Activity, from Peroxidase.

Abstract 009342695 of WO 93100115 A1 published Jan. 7, 1993 entitled Adhesive Patch for Controlled Release of Vapours to Surroundings—Useful for Therapeutic Agents, Insecticides, Insect repellants, Perfumes, etc.

Abstract 009382714 of WO 9302717 A1 published Feb. 18, 1993 entitled Adhesive Prod. Used as Surgical or Medical Dressing—Comprises Emulsion Adhesive Contg. Medicament, Coated on Support, Giving Good Antimicrobial Activity.

Dialog Abstract 009440678 of WO 9306921 A1 published Apr. 15, 1993 entitled Particles with Internal Lyotropic Liq. Crystalline and Lamellar Surface Phases–Form Stable Dispersions Useful for e.g. Sustained Drug Delivery, Antigen Presentation, Nucleic Acid Transport etc.

Dialog Abstract 010298861 of WO 9513704 A1 published May 26, 1995 entitled Material for Sustained Release of Antimicrobial Metal, Esp. Silver—has Atomic Disorder so that Ions etc., are Released into Electrolytes at Increased Rate, Useful e.g. for Coating Medical Devices.

Dialog Abstract 010426917 of WO 9524430 A2 published Sep. 14, 1995 entitled New Block and Graft Copolymers—Comprising pH–Sensitive and Temp. Sensitive Polymer components, Useful for Drug Delivery for Sustained and Controlled Release.

Abstract Document No. 5595750 published Jan. 21, 1997 entitled Antimicrobial Particles of Silver and Barium Sulfate or Zinc Oxide.

Abstract Document No. 5869073 published Feb. 9, 1999 entitled Antimicrobial Liquid Compositions and Methods for Using Them.

Dialog Abstract 010936562 © of WO 9628141A1 published Sep. 19, 1996 entitled Muco–Adhesive Granules Contg Carbomer and Inert Filler—for Sustained Release of Pharmaceutical in Grastro–intestinal Tract.

Dialog Abstract 011905997 © 1999 of WO 9824007A published Jun. 4, 1998 entitled Single Line Automated Fluid Delivering Method for Dental Unit Water Line Treatment—Involves Locking out Operating Control of Consumable Water or Aqueous Solution Delivery Device to Prevent Operation of Device During Antimicrobial Flushing.

Dialog Abstract 008128186 © 1999 of ZA 8809601A published Oct. 25, 1989 entitled Implants Contg. Antimicrobial Agent for Slow Release in Animals.

Dialog Abstract 02495825/g © 1999 entitled AK Steel Signs Pact for Healthier Coating.

Publication by Wipex entitled Disinfectant Wipes with Indicator Stripes.

Article published in Letters in Applied Microbiology 1993, vol. 16, pp. 173–177 entitled An In–Use Study of the Relationship Between Bacterial Contamination of Food Preparation Surfaces and Cleaning Cloths.

Article published in Journal of Applied Bacteriology 1990, Vol 68, p. 271–278 entitled The Survival and Transfer of Microbial Contamination via Cloths, Hands and Utensils.

Article published in J Antibact. Antifungi Agents, vol. 22, No. 9, p. 531–536, 1994, entitled Antimicrobial Activities of Silver and Copper Ions.

Article published by BF Goodrich in http://www.bfsolutions.com entitled Hycar Reactive Liquid Polymers—The Key To Building Superior Products.

Article published by Sybron Chemicals, Inc. of Birmingham, NJ entitled XAMA–7 and Ionac Polyfunctional Aziridine.

Article adapted from Standard Methods for the Examination of Water and Wastewater (method 8167).

Article published in Springer–Verlag Berlin Heidelberg New York 1980 by Erich Lueck entitled Antimicrobial Food Additives—Characteristics—Uses—Effects.

Abstract of Article published in Hy–LITE Data Logger Operators Manual by EM Science.

Abstract of Article published by Hy–LITE by EM Science entitled Hygiene Monitoring in Place.

* cited by examiner

US 6,794,318 B2

USE-DEPENDENT INDICATOR SYSTEM FOR ABSORBENT ARTICLES

The present invention is based on provisional patent application Ser. No. 60/173,344 filed Dec. 28, 1999, and priority is hereby claimed therefrom.

FIELD OF THE INVENTION

The present invention generally relates to an indicator system that can detect the depletion of a variety of chemicals. More particularly, the present invention is directed to a visual indicator system that can be employed in use-dependent products to detect either the exhaustion or depletion of a chemical included therein. For example, the color indicator system of the present invention can be employed in food service wipers to detect the depletion of chemicals, such as anti-microbial agents.

BACKGROUND OF THE INVENTION

A use-dependent device or product is normally considered to be a product that becomes less effective over time. The decline in effectiveness of a particular use-dependent product can be caused by a variety of factors. One such factor that is significant in many applications is the depletion of an active chemical incorporated within the product. For example, wipers, such as those used in medical and food service applications, may contain an anti-microbial agent that is released during wiping to create a solution for disinfecting the surface being wiped. The anti-microbial agent helps prevent potentially harmful microorganism contamination when wiping a particular surface.

Typically, a user of a use-dependent product will want to know when the chemical within the product has been exhausted so that the user can discard the depleted product and begin to use a new one. If no such method is available for determining when the chemical has been exhausted, a user will unknowingly continue to use a product that has been rendered ineffective. For example, in the food service industry, it would be important to determine when an anti-microbial agent of a wiper has been exhausted so that it will not continue to be used thereafter.

In the past, various systems have been developed to indicate variables such as lapses in time, the presence of chemicals, or the absence of chemicals. For example, time indicators, such as disclosed in U.S. Pat. No. 5,699,326 to Haas et al., have been developed to communicate a lapse in time through the use of a visual change in color. Other time indicators are disclosed in U.S. Pat. No. 5,317,987 to Muller et al. and U.S. Pat. No. 4,248,597 to McNeely. In addition to indicators that reveal a lapse in time, indicator systems that detect the presence or absence of a chemical have also been developed. For example, U.S. Pat. No. 4,205,043 to Esch et al. discloses a system that employs a color-sensitive gas to detect the presence of chlorine dioxide.

Besides the above indicator systems, other indicators have been developed to detect the absence of a chemical within a use-dependent product, such as a sanitizing or anti-microbial wiper. For example, an anti-microbial wiper has been marketed by Pal International Inc. of England under the name WIPEX. According to the sales literature, this wiper contains an anti-microbial agent to sanitize various surfaces. In addition, the wipers include indicator stripes that are stated to fade gradually as the disinfectants are depleted. It is believed that U.S. Pat. No. 4,311,479 to Fenn et al. is related to this particular anti-microbial cloth. This indicator system, however undesirably reduces the hydrophilic nature of the wiper.

As such, a need currently exists for a more effective indicator system for use in use-dependent products. In particular, a need exists for an indicator system that can be incorporated into articles containing chemicals such as anti-microbial agents, without having a substantial adverse effect on the properties of the chemicals. Examples of such articles include anti-microbial and/or sanitizing wipers.

SUMMARY OF THE INVENTION

Accordingly, an object of the present invention is to provide an improved use-dependent indicator system.

It is another object of the present invention to provide an indicator system that can signal the depletion of a chemical incorporated within an absorbent article.

Still another object of the present invention is to provide an indicator system that can signal the depletion of a chemical incorporated within an absorbent article without having a substantial adverse affect on the properties of the article that are provided by the chemical.

Yet another object of the present invention is to provide an indicator system containing at least one dye component.

Another object of the present invention is to provide an indicator system containing reactive and/or non-reactive dyes.

It is another object of the present invention to provide an indicator system containing a dye component(s) that can dissolve faster than an active chemical such that the dissolution of the dye can signal the impending exhaustion of the active chemical.

Still another object of the present invention is to provide an indicator system that contains a polymer mixture.

Yet another object of the present invention is to provide an indicator system that contains a polymer mixture that can retain its strength and adhesion properties after being applied to a web, and thereafter creped and cured.

Another object of the present invention is to provide an article in which less than 60% of one side of a cloth-like web is printed with the indicator system.

It is another object of the present invention to provide an indicator system that can provide sufficient control over the dissolution rates of the dye component(s) such that the system can effectively signal the depletion of the active chemical.

These and other objects of the present invention are achieved by providing an absorbent article such as a nonwoven web to which an indicator system of the present invention can be applied. An indicator system of the present invention generally includes at least one dye component and a polymer mixture.

In accordance with the present invention, any material commonly used in the art to manufacture cloths, such as wipers, can be used as the base web. In particular, a base web of the present invention is typically made from a nonwoven polymeric or paper-based web. More particularly, a base web of the present invention can be made from pulp fibers, synthetic fibers, thermomechanical pulp, or mixtures thereof such that the web has cloth-like properties. For instance, the base web can be made from softwood pulp fibers, such as Northern softwood kraft fibers, redwood fibers and pine fibers. Moreover, the base web can also include staple fibers, such as polyolefin fibers, polyester fibers, nylon fibers, polyvinyl acetate fibers, cotton fibers, rayon fibers, non-woody plant fibers, and mixtures thereof. In one embodiment, a base web of the present invention can also be webs that have been subjected to post treatment process such as hydroentanglement. In addition, the web can be a co-form material such as disclosed in U.S. Pat. No. 4,100,324 to Anderson et al. and U.S. Pat. No. 5,350,624 to Georger et al., which are incorporated herein in their entireties by reference thereto.

After forming the base web, an indicator system of the present invention can be applied. In general, the indicator system contains at least one dye component and a polymer mixture. Depending on the application, a single dye or combination of dyes can be used. In one embodiment, the indicator system includes a non-reactive dye, such as a foodstuff dye, that can dissolve out of an article to which it is applied. In other embodiments, the indicator system can include a reactive dye, such as a cationic dye, combined with a non-reactive dye. A reactive dye is typically permanent and will not dissolve out of the article. The combination of dyes selected generally depends on whether the article is desired to retain a color after the active chemical therein has been exhausted.

An absorbent article of the present invention also includes an active chemical, which is used for a variety of reasons. The active chemical can be applied to the article separately, or as part of an indicator system of the present invention. In one embodiment, the active chemical is incorporated within the indicator system as an anti-microbial agent used in wipers. In general, the active chemical within an article will become depleted and will eventually be exhausted after repeated use.

In certain embodiments, the indicator of the present invention will be incorporated into a wiper capable of providing liquid anti-microbial solution after numerous rinse cycles. Such a wiper will generally include a controlled release anti-microbial formulation comprising an anti-microbial agent, which formulation is adhered to an absorbent, cloth-like web which retains liquid after each rinse cycle. The combination of the anti-microbial formulation and the retained liquid in the wiper is adapted so that the formulation releases sufficient anti-microbial agent into the retained liquid after each of at least five normal rinse cycles so that the retained liquid is an anti-microbial solution.

In certain embodiments, the anti-microbial formulation can include an anti-microbial agent encapsulated in, adsorbed to, or as a part of a particle or microcapsule. In certain embodiments, the anti-microbial formulation may be in the form of an anti-microbial agent that is coated by or enclosed in a polymer coating.

As stated, an indicator system of the present invention can also contain a polymer mixture. In some embodiments, a polymer mixture of the present invention can "bloom" or swell in water. In general, a water-swellable polymer mixture of the present invention can contain a variety of components, such as a polymer. For instance, in one embodiment, the polymer mixture can comprise a polymer that is itself water-swellable. Any such water-swellable polymer, such as adhesives, are suitable for use in the present invention. Examples of adhesives that are suitable for use in the present invention include acrylates, styrene butadiene, vinyl chlorides, methacrylates, acrylics (such as carboxylated acrylics), and vinyl acetates (such as self cross-linking ethyl vinyl acetate, hydrolyzed polyvinyl acetate, or non-cross-linking ethyl vinyl acetate). In certain embodiments, the adhesive is made from carboxylated acrylics.

In certain embodiments of the present invention, the polymer mixture can comprise polymers that can become cross-linked. The use of cross-linked polymers, such as latex adhesives, can facilitate control of the dissolution rate of the dye component(s) and/or other chemicals. Specifically, increasing the amount of cross-linking in the adhesive results in less swelling, which in turn, can result in a slower release of the dye components and/or other chemicals into the liquid.

In accordance with the present invention, other various components can also be added as part of the polymer mixture as desired. For example, plasticizers, such as glucose triacetate, can be added to aid in the migration of the active chemical, such as an anti-microbial agent, to the polymer surface. In addition to plasticizers, cross-linking agents, catalysts, plasticizers, thickeners, defoamers, water, and the like, can also be added to a polymer mixture of the present invention. Furthermore, chemicals such as stabilizers, viscosity modifiers, composite particles, or surfactants, can be added as well.

Once an indicator system has been formed in accordance with the present invention, it can then be applied to the base web. Generally, an indicator system of the present invention can be applied to the base web as a chemical formulation by any commonly used method of application, including, but not limited to, print, print crepe, spray, blade, saturant, coating, droplet throw, and foam application methods. For instance, a system of the present invention can be applied as a saturant system, such as disclosed in U.S. Pat. No. 5,486,381 to Cleveland et al., which is incorporated herein in its entirety by reference thereto. Moreover, in another embodiment, the formulation may be printed onto one or both sides of the base web. In some embodiments, the indicator system can also be printed onto the base web as a chemical formulation in a preselected pattern.

The preselected pattern used to apply the indicator system formulation can be, in one embodiment, a reticular interconnected design. Alternatively, the preselected pattern can comprise a succession of discrete shapes, such as dots. In a further alternative embodiment of the present invention, the preselected pattern can be a combination of a reticular interconnected design and a succession of discrete shapes.

The indicator system applied to the base web can generally be applied in a preselected pattern that covers less than 100%, and more particularly from about 10% to about 60% of the surface area of each side of the web. For instance, in one embodiment, the indicator system can be applied as a stripe or other shape to at least one side of the base web.

The indicator system can also be applied to each side of the base web in an amount of from about 2% to about 8% by weight. Once applied, the indicator system can penetrate the base web in an amount from about 10% to about 60% of the total thickness of the web.

In some embodiments, after applying the indicator system to the base web, the web can then be creped to increase the softness, absorbency, and bulk of the web. Depending on the application, one or both sides of the web can be creped. Furthermore, the base web can be dried and cured after applying the indicator system. Curing can increase the strength of the base web, as well as aid in controlling the dissolution rate of the dye component(s) and/or other chemicals. In particular, controlling the degree of polymer curing can, in one embodiment, provide further control over the amount of swelling, which can, in turn, provide control over the dissolution rate of the dye component(s) and/or other chemicals.

In general, an indicator system of the present invention can include various mechanisms, such as a polymer mixture, curing methods, application methods, etc. to control the rate of dissolution of the dye component(s) and/or active chemical. By controlling the rate of dissolution in this manner, the indicator system can signal the complete exhaustion or the gradual depletion of the active chemical. In particular, the rate that a dye component dissolves out of an article can be controlled in a manner such that it dissolves from the article just prior to the active chemical. Therefore, due to a loss in dye, the article will lose or change color. Such a change or loss in color signals to a user the impending or complete exhaustion of the active chemical therein.

Other objects, features and aspects of the present invention are discussed in greater detail below.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In general, the present invention is directed to a use-dependent indicator system that can be effectively incorporated into an absorbent article without having a substantial adverse affect on its properties. For example, it has been discovered that an indicator system of the present invention can detect the depletion of an anti-microbial agent from a wiper that has been repeatedly wetted, rinsed, washed and/or reused without substantially adversely affecting the absorbency of the wiper or the release of the anti-microbial agent.

In accordance with the present invention, a use-dependent indicator system is provided that can be applied to an absorbent article to detect the depletion of a chemical incorporated therein. In one embodiment, an indicator system of the present invention includes the application of a dye or combination of dyes to an absorbent material.

An absorbent article of the present invention generally includes a base web to which dye component(s) and other materials are applied. The base web can be made from any absorbent material commonly used in the art, such as materials used to make food service or medical wipers. In particular, any nonwoven polymeric or paper-based, generally absorbent, web is suitable for use as a base web of the present invention.

A base web of the present invention can be made from pulp fibers, synthetic fibers, and mixtures thereof such that the web has cloth-like properties. For example, the material used to make a cloth-like base web of the present invention can include pulp fibers either alone or in combination with other types of fibers. The pulp fibers used in forming the base web may be softwood fibers having an average fiber length of greater than 1 mm, and particularly from about 2 to 5 mm, based on a length-weighted average. Such fibers can include Northern softwood kraft fibers, redwood fibers and pine fibers. Secondary fibers obtained from recycled materials may also be used.

In one embodiment, synthetic fibers, such as staple fibers (and filaments) can be also added to increase the strength, bulk, softness and smoothness of the base web. Staple fibers can include, for instance, polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have average fiber lengths of 5 mm and greater.

The staple fibers added to the base web can also include bicomponent fibers. Bicomponent fibers are fibers that can contain two materials such as, but not limited to, in a side-by-side arrangement or in a core and sheath arrangement. In a core and sheath fiber, generally the sheath polymer has a lower melting temperature than the core polymer. For instance, the core polymer, in one embodiment, can be nylon or a polyester, while the sheath polymer can be a polyolefin such as polyethylene or polypropylene. Such commercially available bicomponent fibers include CEL-BOND® fibers marketed by the Hoechst Celanese Company.

The staple fibers used in a base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the Z-direction, as well as increase web strength properties.

In general, base webs made according to the present invention can be made exclusively from synthetic fibers, such as fibers made from various polymeric materials. The synthetic fibers can be staple fibers or other various types of fibers or filaments. As described above, a base web of the present invention can also be made from a mixture of staple fibers and pulp fibers. In addition, the web can be a co-form material such as disclosed in U.S. Pat. No. 4,100,324 to Anderson et al. and U.S. Pat. No. 5,350,624 to Georger et al., which are incorporated herein in their entireties by reference thereto. The wipers may be packaged and made according to the disclosures of U.S. Pat. No. 4,833,003 and U.S. Pat. No. 4,853,281 to Win et al.

In one embodiment, when forming an absorbent article containing pulp fibers, the staple fibers can be added to the base web in an amount from about 5% to about 30% by weight and particularly from about 10% to about 20% by weight. For example, short staple fibers made from a polyester or polyolefin can be added to the base web. The fibers can have a length of from about ¼ of an inch to about 1 inch. The fibers can be mixed homogeneously with the pulp fibers in forming the web. Staple fibers can increase the strength and softness of the final product.

Thermomechanical pulp fibers can also be added to the base web. Thermomechanical pulp, as is known to one skilled in the art, refers to pulp that is not cooked during the pulping process to the same extent as conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, the thermomechanical pulp can be added to the base web in an amount from about 10% to about 30% by weight. When using thermomechanical pulp, a wetting agent may be added during formation of the web. The wetting agent can be added in an amount less than about 1% and, in one embodiment, can be a sulphonated glycol.

The fiber furnish used to form the base web can also be treated with a chemical debonding agent to reduce inner fiber-to-fiber strength. Suitable debonding agents that may be used in the present invention when the base web contains pulp fibers include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun, which is incorporated herein by reference.

In a certain embodiment, the debonding agent can be an organic quaternary ammonium chloride. In this embodiment, the debonding agent can be added to the fiber slurry in an amount from about 0.1% to about 1% by weight, based on the total weight of fibers present within the slurry.

In one embodiment, a base web of the present invention as described above can be hydraulically entangled (or hydroentangled) to provide further strength. Hydroentangled webs, which are also known as spunlace webs, refer to webs that have been subjected to columnar jets of a fluid that cause the fibers in the web to entangle. Hydroentangling a web typically increases the strength of the web. Thus, according to the present invention, in order to increase the strength of a web, a base web of the present invention can be hydroentangled. For example, in a certain embodiment, the base web can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wis. HYDROKNIT® is further disclosed in U.S. Pat. No. 5,284,703 to Everhart et al. which is incorporated herein in its entirety by reference thereto.

In accordance with the present invention, a use-dependent indicator system of the present invention can be applied to the base web. The web may be a wiper or other absorbent material capable of absorbing a liquid and then forming a disinfecting solution when rinsed with repeated liquid cycles. In these embodiments, an anti-microbial formulation is applied to a base web such that the anti-microbial agent can be released from the anti-microbial formulation at a controlled rate until the anti-microbial agent is exhausted. When the subject wiper is contacted with water, a certain amount of water is absorbed by the absorbent web and, when the wiper is wrung out, or permitted to drip until excess water has been lost, the absorbent web retains a certain amount of liquid. The anti-microbial agent can be released at a controlled rate to bring the content of the anti-microbial agent in the retained liquid to a level where the retained liquid can act as an anti-microbial solution. Sufficient antimicrobial agent can be incorporated into the anti-microbial formulation and a sufficient amount of the formulation can be adhered to the web, so that only a part of the antimicrobial agent is released from the formulation during each normal rinse cycle and the wiper can continue to provide the retained liquid as an anti-microbial solution after multiple rinsing cycles.

In certain embodiments, a silver-zeolite complex can be utilized as the anti-microbial formulation to provide controlled release of the anti-microbial agent—silver ions. One commercially available example of such a controlled-release silver formulation is sold as a fabric by AgION™ Technologies L.L.C. under the name GUARDTEX®, and is constructed from polyester and rayon and contains a silver-zeolite complex. Other suitable silver-containing anti-microbial agents are disclosed in Japanese Unexamined Patent No. JP 10/259325, which is incorporated herein by reference. Moreover, in addition to silver-zeolites, other metal-containing inorganic additives can also be used in the present invention. Examples of such additives include, but are not limited to, copper, zinc, mercury, antimony, lead, bismuth, cadmium, chromium, thallium, or other various additives, such as disclosed in Japanese Patent No. JP 1257124 A and U.S. Pat. No. 5,011,602 to Totani et al., which are incorporated herein by reference. In some embodiments, the activity of the anti-microbial agent can be increased, such as described in U.S. Pat. No. 5,900,383 to Davis et al., which is also incorporated herein by reference.

The anti-microbial formulation can also be formed by combining an anti-microbial agent with a polymer or a mixture of polymers. Such a formulation can provide controlled release characteristics for the anti-microbial agent by controlling the properties of the polymer, and how the polymer/anti-microbial agent formulation is applied to the base web. For example, such a formulation may be simply particles of an anti-microbial agent that are mixed into a polymer prior to applying the polymer/agent mixture to the web. The polymer can then be cured or cooled to form a solid. The reduced rate of mass transfer of the agent through the solidified polymer provides the method of controlling the rate of release of the agent. Almost any form of an anti-microbial agent can be used with a polymer, including powders, microspheres, controlled-release formulations as described above, gels, liquids, or the like.

The release rate of anti-microbial agents that are a part of a polymer matrix can also be controlled by varying particle size, using polymerization chemistries, encapsulation, using porous absorbents, using soluble binders, and other similar technologies can be employed to enhance the ability to control the amount of anti-microbial agent released over a given period of time.

In another embodiment, the use-dependent indicator system contains a mixture of a polymer mixture and at least one dye component. In such an embodiment, a polymer mixture of the present invention is capable of swelling or "blooming" when contacted with water. In some cases, such "blooming" of the polymer mixture can enhance the control over the release of the dye component(s). As such, in one embodiment, the polymer mixture can comprise any of a variety of materials, at differing amounts, as long as the overall mixture is capable of swelling so as to enhance the control over the release of the dye component(s) contained within the indicator system.

For instance, in one embodiment, the polymer mixture can contain a polymer. Although not required, the polymer itself can be water-swellable to aid in controlling the release of the anti-microbial agent from the base web. Typically, a water-swellable polymer utilized in the present invention can be any polymer capable of swelling in water. For example, various adhesives can be used as water-swellable polymers in the present invention. Examples of adhesives that can be used in a polymer mixture of the present invention include, but are not limited to, acrylates, styrene butadiene, vinyl chlorides, methacrylates, acrylics (such as carboxylated acrylics), and vinyl acetates (such as self cross-linking ethyl vinyl acetate, hydrolyzed polyvinyl acetate, or non cross-linking ethyl vinyl acetate). In certain embodiments, the adhesive can comprise a carboxylated acrylic, such as HYCAR-brand acrylic carboxylated latex.

It should be noted that although most adhesives are suitable for use in accordance with the present invention, some adhesives may not be suitable when used in combination with particular chemicals and/or dyes. For example, anionic latex adhesives may be ineffective when used in combination with certain anti-microbial agents, such as quats, Triclosan, or silver-coated zeolite, which are discussed in greater detail below. However, such adhesives may be completely suitable when used in conjunction with other chemicals.

In some embodiments of the present invention, the polymer may also be a polymer that can becomes cross-linked when dried. A cross-linkable polymer can provide increased wet strength to the base web and can aid in controlling the release time of an anti-microbial agent contained within the formulation. For example, in one embodiment, a liquid latex adhesive capable of becoming cross-linked can be utilized within the polymer mixture. In this embodiment, cross-linking the latex adhesive can provide control over the degree of water-swelling, which can thereby control the amount of the dye component(s) released when the wiper is contacting by a liquid during wiping. For example, in one embodiment, by reducing the amount of adhesive swelling, the relative amounts of a dye component(s) and of an anti-microbial agent released from a wiper in a given period of time is also reduced. In one embodiment of the present invention, the cross-linkable adhesive can be styrene butadiene. In an alternative embodiment, the adhesive can comprise an ethylene vinyl acetate copolymer.

In some embodiments, a cross-linking agent or catalyst can be added to the polymer mixture to aid in cross-linking the polymer. By varying the amount of cross-linking agent or catalyst utilized, the degree of cross-linking can vary, and thus, the release of the dye component(s) can be further enhanced. For example, in one embodiment, an ethylene vinyl acetate copolymer can be cross-linked with N-methyl acrylamide groups using an acid catalyst. Suitable acid catalysts include ammonium chloride, citric acid, maleic acid, and Arizidine catalysts. The carboxylated acrylics are one example of cross-linkable adhesives.

In general, it is often useful to add various other additives to the polymer mixture to enhance surface migration and control over the release time of the anti-microbial agent. For example, a polymer mixture of the present invention can also contain plasticizers to enhance the migration of the dye component(s) to the polymer surface such that it can be more easily removed when during use. One suitable plasticizer includes, for example, glucose triacetate. Moreover, in some embodiments, a polymer mixture of the present can also contain various other components, such as thickeners, defoamers, water, and the like, all of which are well known additives.

Further, other additives, such as composite particles, viscosity modifiers, stabilizers, or surfactants can also be added. Composite particles can generally be added to the polymer mixture to increase the adhesive strength of the polymer mixture without adversely interfering with the other properties of the mixture. Examples of some composite particles that can be used include clay, titanium dioxide, talc, zeolite, silica, or mixtures thereof. Moreover, as stated, one or more stabilizers can be used in the polymer mixture to prevent agglomeration and to increase the stability of the suspension. Stabilizers that may be added to the polymer mixture include cellulose derivatives, such as hydroxy ethyl cellulose or methyl hydroxy cellulose. Other stabilizers that may be used include water-soluble gums, acetates, such as polyvinyl acetate, and acrylics. As stated, the polymer mixture can also contain one or more surfactants. For most applications, nonionic surfactants are preferred.

In accordance with the present invention, a use-dependent indicator system also contains at least one dye component that can dissolve out of an article in which it is incorporated. In particular, one type of dye component used in the present invention is configured in a manner such that it can dissolve out of a base web when the active chemical within the absorbent article therein is substantially depleted or so that it can dissolve out of the web as the active chemical is being depleted from the article. In one embodiment of the present invention, a single dye component is incorporated into a wiper such that the wiper becomes substantially colorless upon depletion of the active chemical. In another embodiment of the present invention, at least two dye components are provided such that the wiper can change color upon depletion of its active chemical.

Dyes of the present invention can generally be made from any dye commonly used in the art to impart a color to an object. Moreover, both a single dye or a combination of dyes can be effectively employed in an indicator system of the present invention. In many circumstances, the selection of a dye type for a particular application can depend on whether that application requires the use of a single dye or a combination of dyes.

For instance, in one embodiment of the present invention, when a single dye is applied to an article, such as an anti-microbial or sanitizing wiper, via an indicator system of the present invention, it imparts color to that article. During use, the dye eventually begins to dissolve out of the article as a chemical therein is depleted. After repeated use, the article continues to lose color and become increasingly lighter until no color remains. At this point, when essentially no color remains, the chemical within the article has been fully exhausted.

As such, when employing a single dye in the present invention as discussed above, it is typically desired that the single dye be capable of dissolving out of the article such that it can signal to a user the exhaustion of a particular chemical. Accordingly, when used alone, a dye of the present invention can be made from any dye capable of dissolving out of an article. In one embodiment, the dye can be a non-reactive dye that is capable of dissolving out of an article to which it is applied after washing and rinsing. Examples of some suitable non-reactive dyes can include, but are not limited to, nonionic or foodstuff dyes, such as blue or green foodstuff dyes.

In addition to employing a single dye, an indicator system of the present invention can also generally employ the use of more than one dye in an article. Generally, multiple dyes can be used for a variety of reasons. One of the reasons for using multiple dyes is the ability to provide an article that can sustain a change in color when a chemical incorporated therein is exhausted. For example, when two dyes are applied to an article via an indicator system of the present invention, different colored dyes can be employed. The differing colors, when originally applied to the article, can impart a certain color to the article. As the article is used and the chemical therein is depleted, one of the dyes begins to dissolve out as described above. Thus, the article changes its color from the combined colors of the multiple dyes to the color of the dye remaining in the wiper after the other dye has dissolved out.

As such, when employing more than one dye in an indicator system of the present invention, it is often desired that one of the dyes be capable of dissolving out of the article. Moreover, when a color change is desired, it is generally required that one of the dyes remain in the article. Thus, in accordance with the present invention, various combinations of non-reactive dyes and/or reactive dyes can be employed as desired. In contrast to a non-reactive dye, a reactive dye is relatively permanent and will not dissolve out of an article to which it is applied upon washing. Examples of some suitable reactive dyes can include, but are not limited to, cationic dyes, sulfur dyes, or pigment dyes.

For example, in one embodiment, a 2% yellow pigment (reactive dye) is mixed with a 4% blue food stuff dye (non-reactive) to form a green sanitizing wiper. As the wiper is used and the sanitizing agent is depleted, the blue dye dissolves out. Eventually, after sustained use, the wiper changes its color to yellow, the color of the reactive dye remaining in the wiper, thereby indicating the substantial exhaustion of the sanitizing agent formerly located within the wiper.

As stated above, an active chemical is typically incorporated with the dye into an absorbent article of the present invention. The active chemical can be added to the absorbent material separately, or as a part of an indicator system of the present invention. One example of an active chemical is an anti-microbial agent used for disinfection. For illustrative purposes, particular anti-microbial agents that can be used in the present invention are described below. However, it should be understood that other active chemicals can also be used in the present invention.

In this regard, an anti-microbial agent of the present invention can generally be made from any anti-microbial additive that can be used as a disinfectant in the art. In most embodiments, an anti-microbial agent of the present invention is made from stationary additives or surface migration additives.

A stationary additive, as that term is used with respect to the present invention, is generally formulated to establish an equilibrium with the respective additive's ions in a water phase. For example, a stationary additive of the present invention can include silver zeolite or coated calcium hypochlorite. A stationary additive made from calcium hypochlorite particles, for example, depends on establishing an equilibrium of the hypochlorite ions in a water phase. Other stationary additives can include, but are not limited to, chlorine dioxide formulations, quaternary amines, halogens, or combinations thereof. In one embodiment, the additive is a chlorine dioxide formulation containing chlorine dioxide, sodium chlorate, and an acid moiety as the anti-microbial agent. Some examples of systems that can be used to generate chlorine dioxide, for instance, are disclosed in U.S. Pat. Nos. 4,681,739; 4,689,169; 5,227,168; 5,126,070; and 5,407,685, which are incorporated herein in their entireties by reference thereto. Another anti-microbial agent that could be employed is disclosed in U.S. Pat. No. 5,837,274 to Shick et al., which is also incorporated herein in its entirety by reference thereto.

As mentioned above, in one embodiment of the present invention, the anti-microbial agent can include silver ions. In this embodiment, a silver-zeolite complex, such as AgION™, can be utilized to provide controlled release of the anti-microbial agent. Moreover, in addition to silver-zeolites, other metal-containing inorganic additives, such as copper, zin, mercury, antimony, lead, bismuth, cadmium, chromium, thallium, etc. can also be used in the present invention.

In addition to various stationary additives, an anti-microbial agent can also be made from surface migration additives. A surface migration additive, as that term is used with respect to the present invention, is generally formulated to migrate to the surface over an extended period of time. For example, suitable surface migration additives can include liquid quaternary ammonium compounds, such as alkyl aryl benzalkonium chloride, or other materials such as Triclosan.

In some applications, it may also be necessary to adjust the pH of the active chemical, dye component(s), and/or the polymer mixture before forming the formulation. In particular, one embodiment of the present invention includes the addition of ammonia to both the polymer mixture and the active chemical such that the pH of each is adjusted to a more neutral value prior to mixing. The added ammonia generally dissipates during the later step of curing, which is discussed in more detail below.

In general, once the polymer mixture and dye component(s) are incorporated into a chemical formulation according to the present invention, the formulation can then be applied to the base web through any known method of application, such as print, print crepe, spraying, blade, saturant, coating, droplet throw, and foam applications. For example, in one embodiment, the formulation can be saturated into the web, such as disclosed in U.S. Pat. No. 5,486,381 to Cleveland et al., which is incorporated herein by reference. Moreover, in another embodiment, the formulation can be printed onto at least one side of the base web, and, in some cases to both outer surfaces of the web. Although any method of application is suitable for use in the present invention, it should be understood that the particular application method utilized can also have an affect on release time of the dye component(s) and/or active chemical. As such, in accordance with the present invention, the method of application can also be selected as desired to further enhance the control over the release time of the dye component(s) and/or active chemical.

In one embodiment of the present invention, the formulation can be applied to the base web in a preselected pattern. For instance, the formulation can be applied to the base web as a stripe. Moreover, the formulation can be applied in a reticular pattern, such that the pattern is interconnected forming a net-like design on the surface. The formulation can also be applied according to a diamond shaped grid. The diamonds, in one embodiment, can be square having a length dimension of ¼ inch. In an alternative embodiment, the diamonds comprising the grid can have length dimensions of 60 mm and 90 mm.

In an alternative embodiment, the formulation can be applied to the base web in a pattern that represents a succession of discrete dots. This particular embodiment is generally well suited for use with lower basis weight wiping products. Applying the formulation in discrete shapes, such as dots, can provide sufficient strength to the base web without covering a substantial portion of the surface area of the web. In particular, applying the formulation to the surface of the base web can, in some instances, adversely affect the absorbency of the web. Thus, in some applications, it may be desired to minimize the amount of formulation applied.

In a further alternative embodiment, the formulation can be applied to the base web according to a reticular pattern in combination with discrete dots. For example, in one embodiment, the formulation can be applied to the base web according to a diamond-shaped grid having discrete dots applied to the web within the diamond shapes.

In one embodiment of the present invention, the formulation can also be applied to one or both sides of the base web so as to cover less than 100% of the surface area of the web, particularly from about 10% to about 60% of the surface area of the web. More particularly, in most applications, the formulation will cover from about 20% to about 40% of the surface area of each side of the base web. The total amount of formulation applied to each side of the base web can range from about 2% to about 10% by weight, based upon the total weight of the base web. Thus, when the formulation is applied to each side of the web, the total add-on will be from about 4% to about 20% by weight.

According to one embodiment of the present invention, after the formulation is applied to the base web, one or both of the outer surfaces containing the formulation can then be creped by known creping processes. Although not required, creping at least one side of the base web may sufficiently disrupt the fibers within the web to increase softness, absorbency, and the bulk of the web.

In one embodiment of the present invention, the base web is first pressed into contact with a creping drum by a press roll. The formulation containing the dye component(s) active chemical, and/or polymer mixture, which has already been applied to the base web, causes only those portions of the web where it has been disposed to adhere to the creping surface. If desired, the creping drum can be heated for promoting attachment between the base web and the surface of the drum, as well as partially drying the base web.

Once adhered to a creping drum, the base web may then be brought into contact with a creping blade that can remove the base web from the creping drum, thereby performing a first controlled pattern crepe on the base web. In applications where the formulation is applied to each side of the base web, the web can also be creped on the second side of the web. In these applications, a second creping blade can perform a second controlled creping operation on the second side of the base web.

In one embodiment of the present invention, after the base web has been applied with the formulation, the base web may then be dried and cured to form a sufficiently strong web. In one embodiment, the base web is pulled through a curing or drying station that can include any form of heating unit, such as an oven energized by infrared heat, microwave energy, hot air or the like. In addition to forming a stronger base web, the process of curing can also aid in controlling the release time of the dye component(s) and/or active chemical. Specifically, by altering the degree of polymer curing, the swelling of the polymer mixture in water can be reduced, thereby decreasing the amount of dye component (s) and/or active chemical released during use.

As described above, an indicator system of the present invention can be configured such that the dissolution rate of the dye component(s) contained within the system can be effectively controlled. For example, the composition of the polymer mixture, degree of water-swelling, cross-linking, curing, plasticizing, method of application, or any other comparable mechanisms, can all provide sufficient control of the dissolution rate of the dye component(s). By effectively controlling the dissolution rate in this manner, an indicator system of the present invention can properly function to indicate the depletion of a particular active chemical. In particular, the rate that the dye component(s) dissolves out of the base web can be controlled in a manner such that dissolution of the indicator dye component occurs just prior to the dissolution of the active chemical itself. As such, a loss or change in color can reveal the impending depletion of the active chemical.

The dissolution rate of other chemicals within an indicator system or article of the present invention can also be controlled. For example, by utilizing the methods of control described above or other comparable methods, the dissolution rate of an active chemical, such as an anti-microbial agent, can be effectively controlled. In some embodiments, the dissolution rate of an anti-microbial agent is controlled in a manner to provide controlled release over a period of time such that the article in which it is incorporated can sustain multiple washing and rinsing operations.

In one embodiment, the dissolution rate of an active chemical of the present invention can also be controlled by various mechanisms relating to the chemical itself. For example, in an embodiment where an anti-microbial agent comprises the active chemical, the solubility of an anti-microbial agent can be varied to control the release time of such particles when activated with water. Methods for varying additive solubility, such as varying particle size and employing anti-microbial agents having a certain size distribution, using polymerization chemistries, encapsulation, using porous absorbents, using soluble binders, and other similar technologies can be employed to enhance the control of the amount of the active chemical released over an extended period of time.

When an active chemical, such as an anti-microbial agent, is coated or encapsulated as mentioned above, any coating known in the art to reduce solubility can be used. For example, in one embodiment, an aqueous emulsion of an acrylic polymer may be used to coat a calcium hypochlorite anti-microbial agent. In another embodiment, a microcrystalline wax coating may be applied to the solid particles. In yet another embodiment, polyethylene can be used. Moreover, to sufficiently reduce solubility when using a coating, it is not generally necessary to completely coat the particles. For instance, in one embodiment, a 20% acrylic polymer coating is used, while in another embodiment, a 33.5% acrylic polymer coating is used. In still another embodiment, a 60% microcrystalline wax coating is used.

The example below demonstrates the ability of an indicator system of the present invention to control dissolution rates. In particular, the following example demonstrates the ability to control the rate that a dye component(s) dissolves out of a base web which comprises an absorbent wiper.

EXAMPLES

Four samples of an absorbent wiper were prepared. In each sample, the indicator system included a reactive dye, non-reactive dye, and latex adhesive. Specifically, a 2% (based on latex solids) reactive yellow pigment, a 4% non-reactive blue food stuff dye, and a Hycar-brand acrylic carboxylated latex were printed onto each wiper to form a green wiper. A different amount of aziridine crosslinking agent was applied to the latex to demonstrate the ability to control the dissolution rate of the dye by cross-linking. The wipers were rinsed until the wiper changed to yellow. The results of the experiment are depicted below:

TABLE 1

| % Cross-linking Agent | # Rinses Required to Change Color to Yellow |
|---|---|
| 0% | 6 |
| 1% | 12 |
| 2% | 20 |
| 4% | Did not wash out after 50 rinses |

As shown in Table 1, the addition of a higher percentage of cross-linking agent produced more cross-linking in the latex adhesive, which in turn lowered the rate that the dye component dissolved out of the wiper. As such, an indicator system of the present invention can be varied in a manner so as to provide the necessary dissolution rates for a dye(s) incorporated therein. In particular, the dissolution rate of the dye(s) can be controlled such that it washes out of the base web prior to the active chemical to signal the depletion of the active chemical.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. An absorbent article containing an active chemical comprising: an absorbent web containing fibers, said absorbent web having at least two outer surfaces; and an indicator system applied to said web, said indicator system comprising at least one dye component imparting a color to said at least one surface, said at least one dye component being capable of dissolving into a liquid when contacted therewith, said at least one dye component dissolving at a faster rate than said active chemical when contacted with said liquid such that said color of said at least one surface becomes altered before said active chemical is completely exhausted during the use of said article; and a cross-linked water-swellable polymer mixture applied to said web, wherein said cross-linked water-swellable polymer is cross-linked to a degree that controls the rate that said at least one dye component dissolves into said liquid when contacted therewith.

2. An article as defined in claim 1, wherein said web has at least two outer surfaces, said indicator system being applied to at least one of said two surfaces.

3. An article as defined in claim 2, wherein said indicator system covers less than about 60% of said at least one surface of said web such that said web is capable of maintaining absorbent properties.

4. An article as defined in claim 1, wherein said indicator system comprises a non-reactive dye.

5. An article as defined in claim 1, wherein said indicator system comprises a reactive dye.

6. An article as defined in claim 1, wherein said polymer mixture comprises a polymer capable of swelling in water.

7. An article as defined in claim 1, wherein said polymer mixture comprises an additive selected from the group consisting of a cross-linking agent, a catalyst, a thickener, a plasticizer, a defoamer, composite particles, a viscosity modifier, a stabilizer, a surfactant, and combinations thereof.

8. An article as defined in claim 1, wherein said active chemical comprises an anti-microbial agent.

9. An article as defined in claim 8, wherein said anti-microbial agent comprises a stationary additive.

10. An article as defined in claim 8, wherein said anti-microbial agent comprises a surface migration additive.

* * * * *

UNITED STATES PATENT AND TRADEMARK OFFICE
CERTIFICATE OF CORRECTION

| | | |
|---|---|---|
| PATENT NO. | : 6,794,318 B2 | Page 1 of 1 |
| APPLICATION NO. | : 09/746719 | |
| DATED | : September 21, 2004 | |
| INVENTOR(S) | : Ralph L. Anderson, James W. Clark and Fred R. Radwanski | |

It is certified that error appears in the above-identified patent and that said Letters Patent is hereby corrected as shown below:

On Title Page, Item (56)
Under US Patent Documents "3,060,078" should be --3,060,079--

On Title Page, Item (56)
Under US Patent Documents "4,102,998 A     7/1978 Gutnick ......... 424/15" should be --4,102,998 A     7/1978 Gutnick......... 424/15--

On Title Page, Item (56)
Under Other Publications an additional PCT Search Report should be listed as International Search Report dated Apr. 18, 2001 for International Application No. PCT/US00/34930.

On Title Page, Item (56)
Under Other Publications "Dialog Abstract 004062594 ... entitled Hygenic Toilet Seat Cover for One-Time Uuse ..." should be --Dialog Abstract 004062594 ... entitled Hygenic Toilet Seast Cover for One-Time Use ...--

On Title Page, Item (56)
Under Other Publications "Dialog Abstract 02495825/g" should be --Dialog Abstract 02495825/9--

Signed and Sealed this

Third Day of April, 2007

JON W. DUDAS
*Director of the United States Patent and Trademark Office*